(12) United States Patent
Hoyns (10) Patent No.: US 6,308,092 B1
(45) Date of Patent: Oct. 23, 2001

(54) OPTICAL FIBER TISSUE LOCALIZATION DEVICE

(75) Inventor: Dirk V. Hoyns, Conyers, GA (US)

(73) Assignee: C. R. Bard Inc., Murray Hill, NJ (US)

( * ) Notice: Subject to any disclaimer, the term of this patent is extended or adjusted under 35 U.S.C. 154(b) by 0 days.

(21) Appl. No.: 09/416,870

(22) Filed: Oct. 13, 1999

(51) Int. Cl.[7] ........................................ A61B 6/00
(52) U.S. Cl. ............................ 600/478; 606/2; 606/15
(58) Field of Search ........................... 600/407, 473, 600/476, 478, 342, 344; 606/2, 3–18

(56) References Cited

U.S. PATENT DOCUMENTS

| | | |
|---|---|---|
| 4,007,732 | 2/1977 | Kvalve et al. . |
| 4,567,882 | 2/1986 | Heller . |
| 5,111,828 | 5/1992 | Kornberg et al. . |
| 5,643,251 * | 7/1997 | Hillsman et al. .................. 606/7 |
| 5,722,426 | 3/1998 | Kolff . |
| 5,782,771 | 7/1998 | Hussman . |
| 6,129,683 * | 10/2000 | Sutton et al. .................. 600/564 |

OTHER PUBLICATIONS

Optical Breast Lesion Localization Fiber: Preclinical Testing of a New Device, *Radiology*, Sep. 1996, pp. 865 and 866.

* cited by examiner

*Primary Examiner*—Brian L. Casler
(74) *Attorney, Agent, or Firm*—Kilpatrick Stockton LLP (57) ABSTRACT

An apparatus for marking a location within the tissue of a patient includes an optical fiber whose forward end illuminates to facilitate localization of a target tissue by a physician. A strain relief tube is disposed around the outer diameter of the optical fiber adjacent the forward end of the optical fiber. An anchor means, such as a pair of hooks, is mounted to the strain relief tube for engaging the tissue of a patient to secure the tip of the optical fiber within the tissue of the patient. The anchor means is deployed to anchor the tip of the optical fiber in the vicinity of a location desired to be marked. The rearward end of the optical fiber is optically coupled to a light source to transmit light through the optical fiber to illuminate the tip, thereby to facilitate a physician in visually locating the tip.

9 Claims, 8 Drawing Sheets

OPTICAL FIBER TISSUE LOCALIZATION DEVICE

TECHNICAL FIELD

The present invention relates generally to guide wires used to localize lesions and relates more specifically to guide wires incorporating optical fibers to facilitate visually locating the forward end of the guide wire.

BACKGROUND OF THE INVENTION

Ultrasound, mammography, magnetic resonance imaging, and other medical imaging modalities are widely used to identify suspicious lesions within the body of a patient. Historically, when a suspicious lesion is located within the body of a patient, a guide wire was inserted by the physician to mark the location of the lesion to enable a surgeon to locate the lesion for removal. The guide wires typically include barbs or hooks at their forward ends to securely anchor the guide within the target tissue.

A problem with such guide wires, however, is that it is sometimes difficult for the surgeon to locate the forward end of the guide wire. While tugging on the guide wire will cause movement at the forward end which the surgeon can visually identify, the tugging action can also dislodge the guide wire from the target tissue. Accordingly, another method of locating the forward end of a guide wire was needed.

To address this problem, the prior art discloses a guide wire fabricated from an optical fiber. Hooks were affixed to the forward end of the optical fiber to anchor the tip of the fiber in the target tissue. The free end of the optical fiber was hooked up to a small laser, and a beam of light was directed through the fiber. A diffuser tip at the forward end of the guide wire created a point of light which could easily be visualized by a surgeon through several centimeters of tissue, thereby facilitating the location of the forward end of the guide wire. U.S. Pat. No. 5,782,771 to Hussman and an article entitled *Optical Breast Lesion Localization Fiber: Preclinical Testing of a New Device* from the September 1996 issue of RADIOLOGY describe the optical fiber localization device in detail.

While this prior art device represents an improvement in terms of locating the forward end of the guide wire without dislodging the guide wire from the tissue, there are significant structural problems inherent in the design of the device. Specifically, the optical fiber incorporates a stepdown portion at the forward tip of the fiber to diffuse the transmitted light. This step-down portion, however, also creates a structural weakness that is exacerbated by the hooks being mounted to the reduced portion. In short, any significant torque on the hooks can cause the tip of the optical fiber to break off.

Thus there is a need for an optical fiber tissue localization device which better resists breakage in response to torque exerted by the hooks.

There is a further need for an optical fiber tissue localization device which meets the foregoing needs while being inexpensive to manufacture.

SUMMARY OF THE INVENTION

Stated generally, the present invention comprises an improved tissue localization device of the type which employs an optical fiber, the forward tip of which is anchored within the target tissue by hooks affixed to the device and illuminates to facilitate localization of the target tissue by the physician. The optical fiber tissue localization device of the present invention better resists breakage of the optical fiber in response to torque exerted by the hooks.

Stated somewhat more specifically, the present invention relates to an apparatus for marking a location within the tissue of a patient. An optical fiber has a forward end shaped into a tapered tip. A strain relief tube is disposed around the outer diameter of the optical fiber adjacent the forward end of the optical fiber. An anchor means is mounted to the strain relief tube for engaging the tissue of a patient to secure the tip of the optical fiber within the tissue of the patient. The anchor means may be deployed to anchor the tip of the optical fiber in the vicinity of a location desired to be marked. The rearward end of the optical fiber is optically coupled to a light source to transmit light through the optical fiber to illuminate the tip, thereby to facilitate a physician in visually locating the tip.

Thus it is an object of the present invention to provide an improved optical fiber tissue localization device.

It is another object of the present invention to provide an improved optical fiber tissue localization device which is less susceptible to breakage resulting from torque exerted by the hooks which anchor the fiber within the target tissue.

Other objects, features, and advantages of the present invention will become apparent upon reading the following specification, when taken in conjunction with the drawings and the appended claims.

BRIEF DESCRIPTION OF THE DRAWINGS

FIGS. 8–10 depict the use of the tissue localization device and cannula assembly of FIG. 7 to mark a suspicious lesion, where:

DETAILED DESCRIPTION OF THE DISCLOSED EMBODIMENT

Reference is now made to the drawings, in which like numerals indicate like elements throughout the several views. In FIGS. 1–5 an optical fiber tissue localization device 10 includes an optical fiber 12. The optical fiber 12 of the disclosed embodiment is 0.04 inches (1 mm) in diameter and has a nominal length of 1 meter. The optical fiber 12 of the disclosed embodiment is a Mitsubishi ELSA-ASK40 fiber optical monofilament, from Mitsubishi International Corporation. The optical fiber 12 has a solid core of acrylic polymer (polymethyl-methacrylate) sheathed with a thin layer of fluorine polymer which has a lower refractive index than the fiber core.

Figure 1:
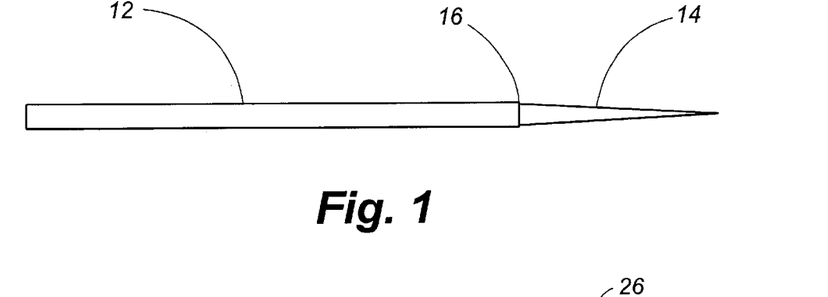
FIG. 1 is a side view of an optical fiber of the tissue localization device of the disclosed embodiment.

The forward end of the optical fiber is ground into a conical tip 14. The conical tip 14 is approximately 0.4 inches (~10 mm) in length and is tapered at an angle of approximately 2°. To facilitate dispersion of light transmitted down the optical fiber 12, the conical tip 14 has a matte finish on its external surface. A junction 16 indicates the location where the rearward end of the conical tip 14 joins the main body of the optical fiber 12.

Figure 2:
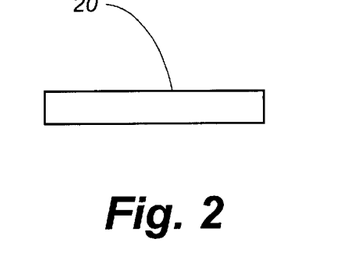
FIG. 2 is a side view of a strain relief tube of the tissue localization device of the disclosed embodiment.
Figure 4:
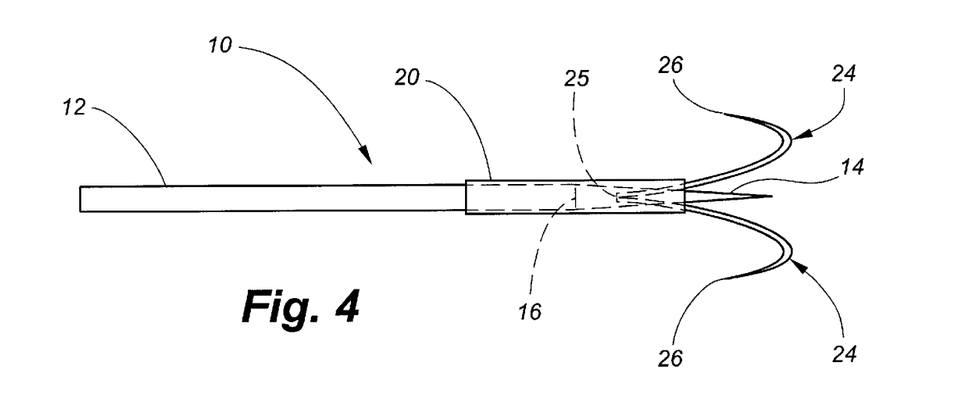
FIG. 4 is a side view of the assembled tissue localization device of the disclosed embodiment.
Figure 5:
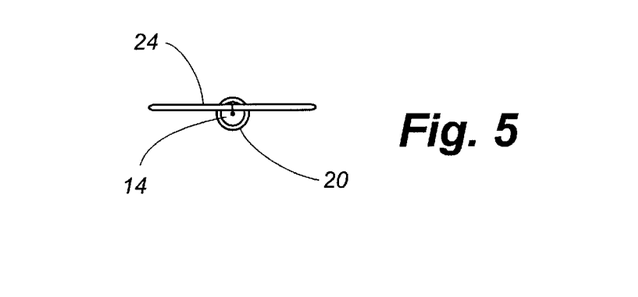
FIG. 5 is a front view of the tissue localization device of FIG. 4.
Figure 6:
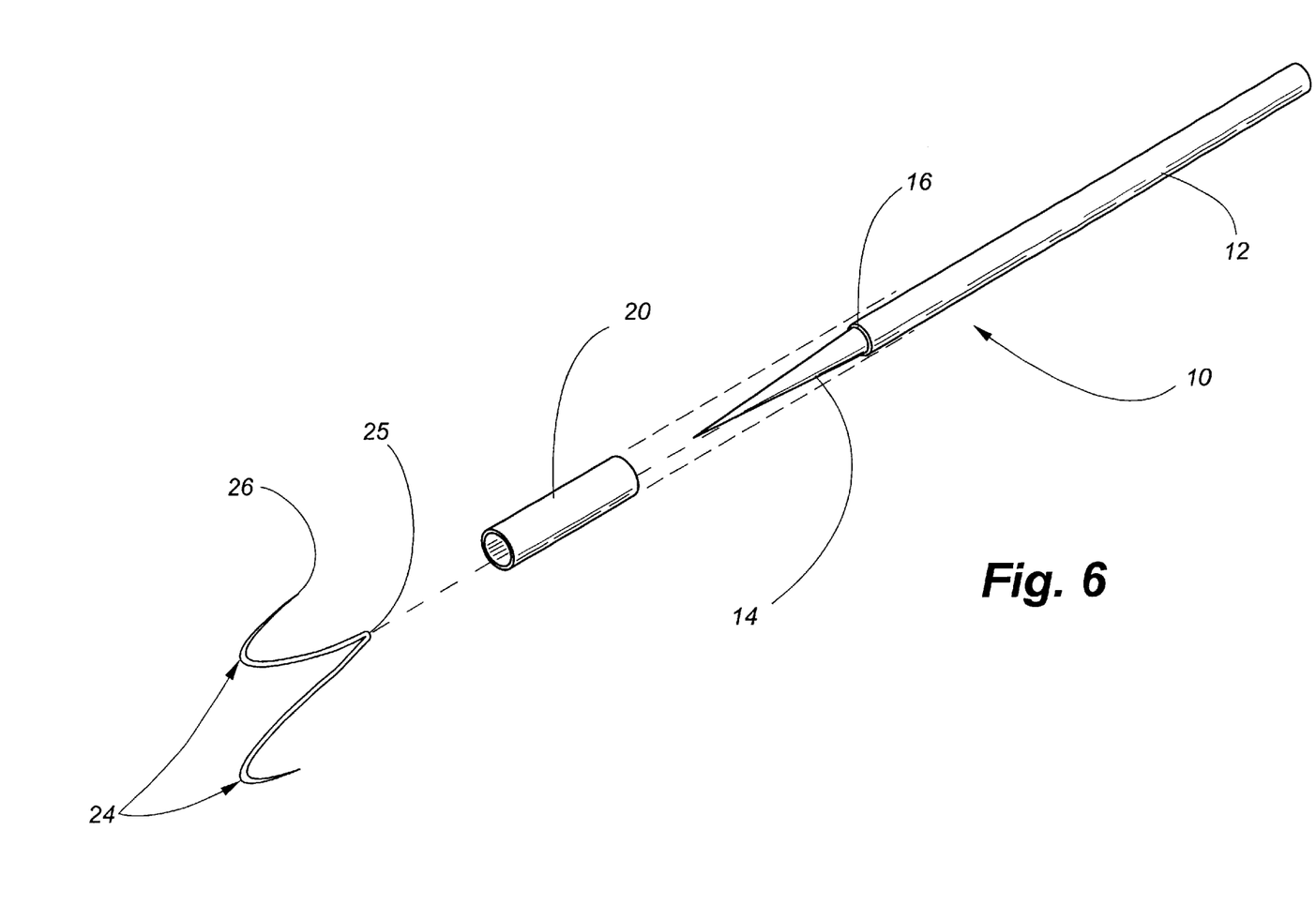
FIG. 6 is an exploded perspective view of the tissue localization device of FIG. 4.

Referring now to FIG. 2, a strain relief tube 20 of stainless steel or other suitable material has an inner diameter of 0.041 inches (1.04 mm) and is approximately 0.4 inches (~10 mm) long. The strain relief tube 20 fits over the forward end of the optical fiber 12, as shown in FIGS. 4–6, and straddles the junction 16 between the fiber and the conical tip 14. In the disclosed embodiment approximately 0.2 inches (5 mm) of the conical tip 14 is exposed beyond the forward end of the strain relief tube 20.

Figure 3:
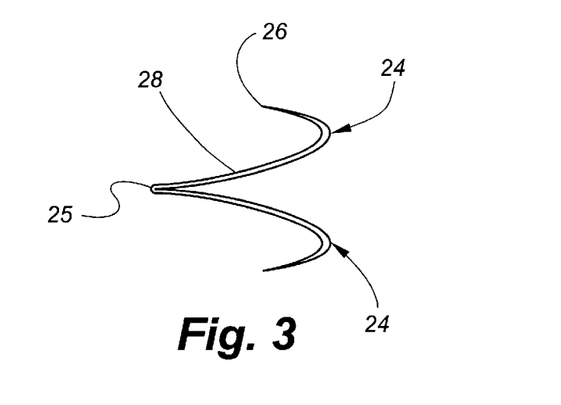
FIG. 3 is a side view of a pair of hook members of the tissue localization device of the disclosed embodiment.

Referring to FIG. 3, the tissue localization device 10 further comprises a pair of hook members 24 comprised of a flexible, resilient material such as 302 stainless steel. In the disclosed embodiment the two hook members 24 are formed from a single piece of wire and are thus joined at their rearward ends 25. Each hook member 24 comprises a barb 26 and a shank 28. To enable the hook members 24 to be temporarily straightened and to return to their original configurations without being permanently deformed, the device 10 is preferably heat-treated at temperatures of approximately 500° C. (932° F.) such that material hardening takes place.

As can be seen in FIGS. 4–6, the hook members 24 are mounted to the forward end of the device 10. More specifically, the rearward ends 25 of the hook members 24 are inserted into the forward end of the strain relief tube 20 and are advanced until they are wedged between the strain relief tube 20 and the conical tip 14 of the optical fiber 12. In this position the hook members 24 are disposed on opposite sides of the device 10 with the barbs 26 projecting outward and rearward. A suitable medical grade adhesive, such as LOCTITE 4014 Medical Device Instant Adhesive from Loctite Corporation, Hartford, Conn., is used to bond the hooks 24, the strain relief tube 20, and the conical tip 14 together.

Figure 7:
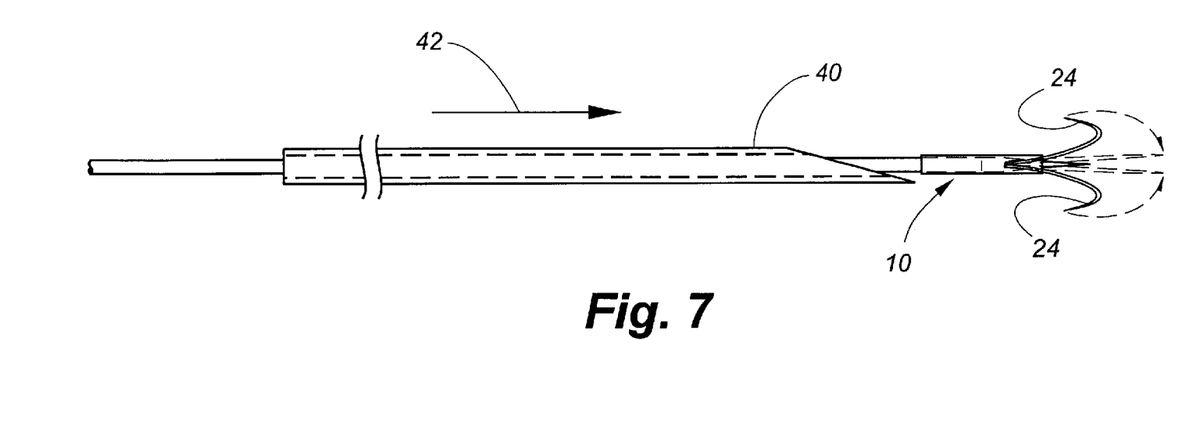
FIG. 7 is a side view showing the loading of the tissue localization device of FIG. 4 into a hollow cannula.

Referring now to FIG. 7, the device 10 is loaded into a hollow cannula 40 by inserting the rearward end of the optical fiber 12 into the forward end of the cannula 40 and advancing the cannula over the length of the optical fiber in the direction indicated by the arrow 42. As the cannula 40 confronts the hook members 24, the hook members are bent forward and inward until the hook members reside within the forward end of the cannula. Preferably this loading of the device 10 into the cannula 40 occurs prior to packaging and shipping the device so that the physician is spared the step of assembling the two components.

Figure 8:
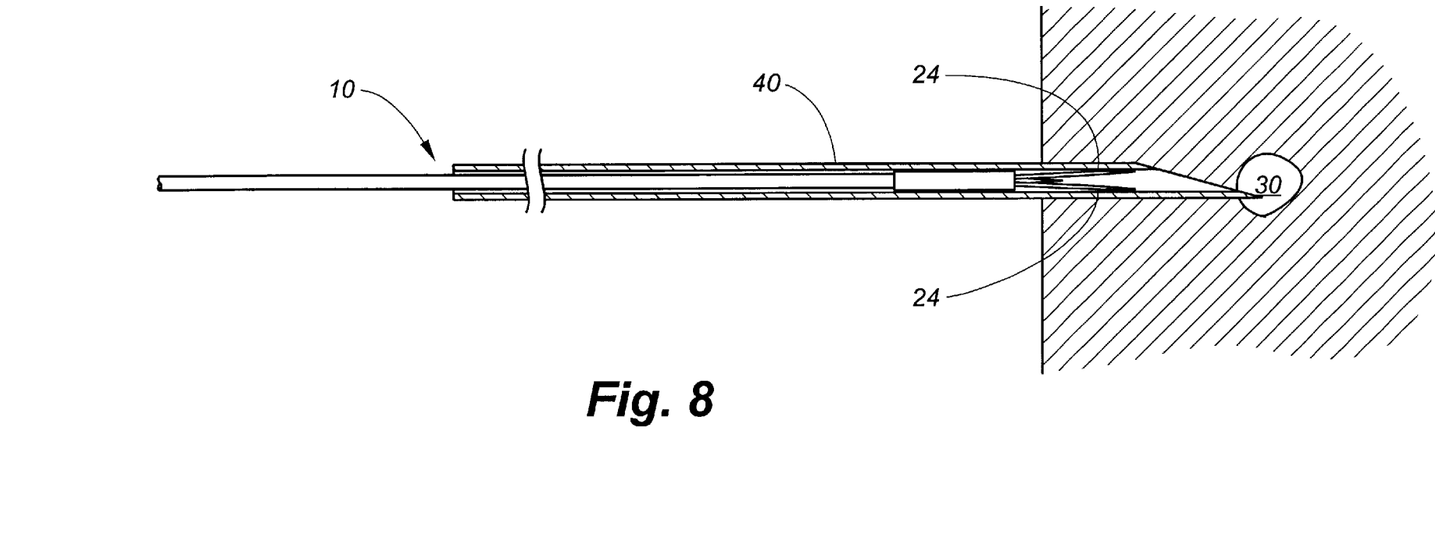
FIG. 8 shows the insertion of the forward end of the cannula into a suspicious lesion.
Figure 9:
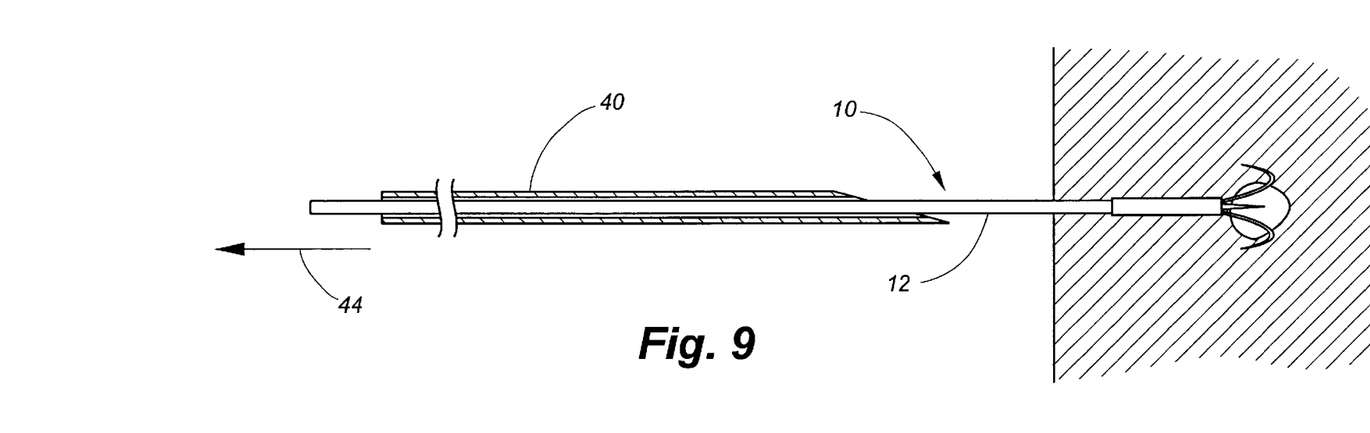
FIG. 9 shows the cannula being withdrawn over the optical fiber and the tip of the tissue localization device anchored within the suspicious lesion.

Operation of the device 10 will now be explained with reference to FIGS. 8–10. When a suspicious lesion 30 (the "target tissue") is located by a medical imaging modality such as ultrasound, mammography, magnetic resonance imaging, CT scan, or the like, the physician inserts the forward end of the cannula 40 into the patient and advances it to a location immediately adjacent the target tissue 30, as shown in FIG. 8. Location of the forward end of the cannula 40 may then be verified by a second imaging procedure.

When proper location of the forward end of the cannula 40 with respect to the lesion 30 has been verified, the cannula is withdrawn over the optical fiber 12 in the direction indicated by the arrow 44. As the cannula is withdrawn to expose the hook members 24, the hook members spring outward, as shown in FIG. 9, and the barbs 26 of the hook members anchor the conical tip 14 of the device 10 within the target tissue 30.

Should it become necessary to reposition the tip 14 of the device, the cannula 40 can be advanced over the optical fiber 12 in substantially the same manner explained above with reference to FIG. 7 to retract the hook members 24. Once the hook members 24 have been retracted within the forward end of the cannula 40, the cannula can be repositioned as needed, at which point the cannula is again withdrawn over the optical fiber 12 to deploy the hook members.

Figure 10:
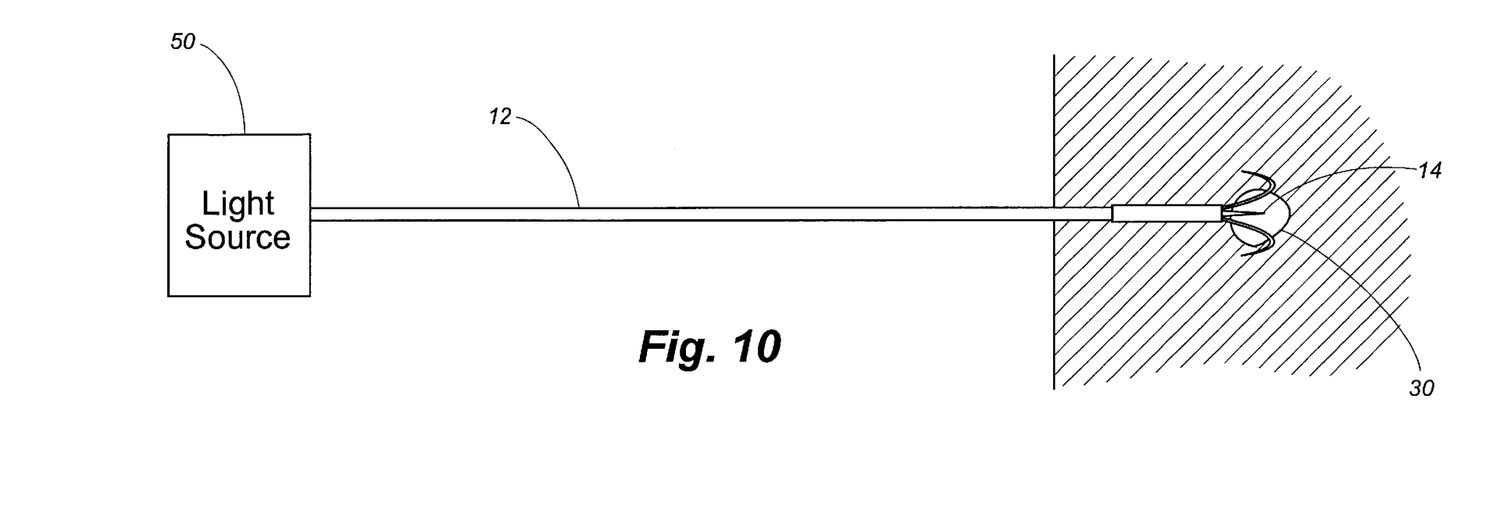
FIG. 10 shows the rearward end of the optical fiber of the tissue localization device hooked up to a light source, with the light source shown schematically.

After the cannula 40 has been withdrawn over the rearward end of the optical fiber 12, the rearward end of the fiber is optically coupled to a light source 50, as shown schematically in FIG. 10. In the disclosed embodiment the light source 50 is a 5 mW, 635 nm wavelength laser, Class 3A, available from C.R. Bard, Inc. A beam of light is transmitted from the light source 50 down the optical fiber 12 and strikes the tip 14, where the matte external surface of the tip disperses the light. The physician can now easily see the tip 14 through several centimeters of tissue, facilitating location of the target tissue.

While the foregoing embodiment is disclosed with respect to a device 10 having a strain relief tube 20 comprised of a rigid material, it will be understood that rigidity is not a prerequisite. Rather, a strain relief tube can be comprised of any material to which the hook members 24 can be bonded, which spreads the force exerted by the hook members 24 over a larger area of the optical fiber 12, and which makes the junction 16 between the tip 14 and optical fiber 12 stronger than it would be otherwise.

As can be seen from the foregoing explanation of the operation of the tissue localization device 10, the cannula 40 must be withdrawn over the rearward end of the optical fiber 12 prior to the fiber being coupled to the light source 50. However, it is also necessary to provide the rearward end of the optical fiber 12 with a means by which to couple the fiber to the light source 50. Since such couplings are conventionally integral with the fiber, these needs are in conflict. To meet these needs, the optical fiber 12 of the disclosed embodiment is coupled to the light source 50, both optically and physically, by means of a quick-connect coupling which can quickly, easily, and reliably be attached to the rearward end of the optical fiber 12 after the cannula 40 has been withdrawn.

Figure 11:
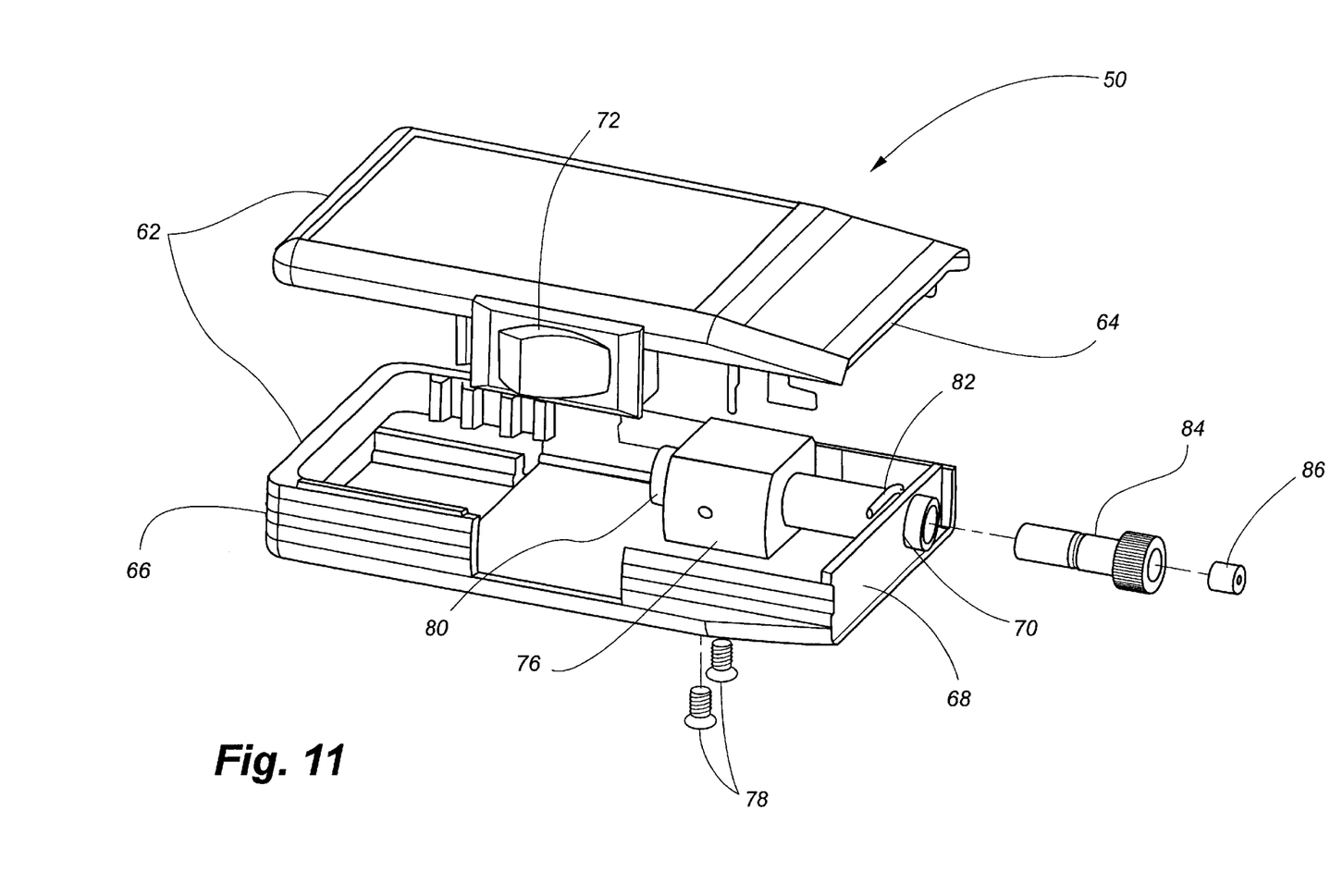
FIG. 11 is an exploded perspective view of the light source which is depicted schematically in FIG. 10.

FIG. 11 is an exploded view of the light source 50, heretofore shown only schematically. The light source 50 includes an enclosure 62, which is an off-the-shelf product (SER PAC Enclosure M6, Serpac, Inc.) with certain modifications, as will be explained below. The enclosure 62 includes an upper housing 64, a lower housing 66, and a front panel 68. The lower housing 66 includes recesses and electrical contacts (not shown) for a pair of "AA" batteries (also not shown), which power a laser, as will be explained.

The enclosure 62, is modified from its off-the-shelf configuration in the following respects. A circular hole 70 is formed in the front panel 68. The upper and lower housings 64, 66 are modified to accept a conventional rocker-type electrical switch 72, which is operable to open or close the electrical circuit powered by the batteries.

Referring further to FIG. 11, the light source 50 further includes a quick-release coupling comprising a mount 76 anchored to the lower housing 66 by means of screws 78. A laser 80, such as Part No. M635-5 from NVG, Inc., Hazelhurst, Ga., is attached to the rearward end of the mount 76. The laser 80 is operatively connected to the electrical circuit powered by the batteries and controlled by the electrical switch 72 so as to illuminate when the switch is activated.

A retainer clip 82 snaps onto the mount 76. An adapter 84 fits into the forward end of the mount 76. A rubber bushing 86 fits into the forward end of the adapter 84. Together, the mount 76, retainer clip 82, adapter 84, and bushing 86 comprise a quick-connect coupling device. Each of these components will be described below in more detail with reference to other drawing figures.

Figure 15:
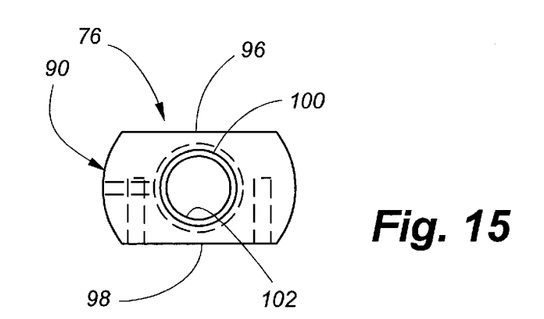
FIG. 15 is a front view of the mount of FIG. 12.

The mount 76 is shown in more detail in FIGS. 12–15. The mount 76 includes a body 90 having a front face 92 and a rear face 94. As can be seen in FIG. 15, the body 90 is shaped like a cylinder with flat upper and lower faces 96, 98.

Figure 12:
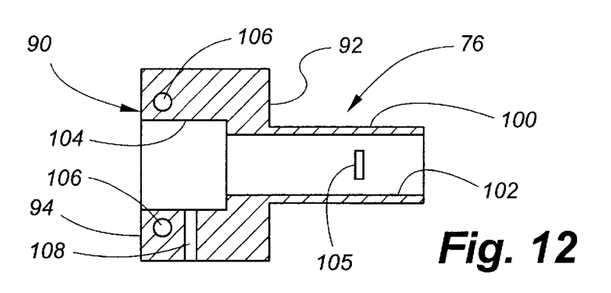
FIG. 12 is a top cutaway view of a mount of the light source of FIG. 11.
Figure 13:
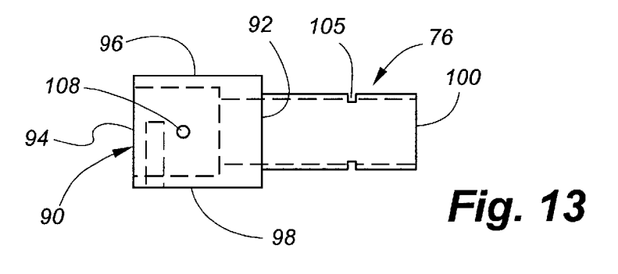
FIG. 13 is a side view of the mount of FIG. 12.
Figure 14:
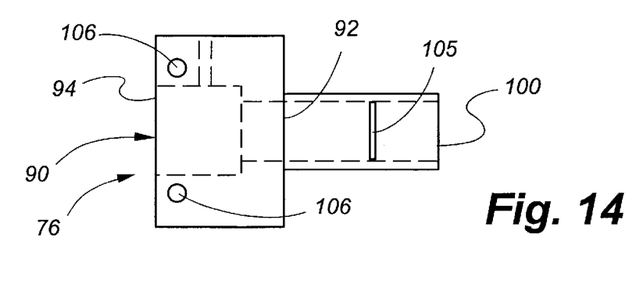
FIG. 14 is a bottom view of the mount of FIG. 12.

The mount 76 further includes a tubular barrel 100 extending forward from the front face 92 of the body 90. A longitudinal through bore 102 extends through the barrel 100 and the body 90. A counterbore 104 having a diameter slightly larger than the through bore 102 is formed in the rear face 94 of the body 90 coaxial with the through bore. More specifically, the counterbore 104 is dimensioned to receive the forward end of the laser 80. Slots 105 are formed through the upper and lower walls of the barrel 100 of the mount 76.

Two vertical threaded bores 106 are formed in the lower face 98 of the body 90 of the mount 76, one on either side of the counterbore 104, to receive the mounting screws 78 (FIG. 11) for anchoring the mount 76 to the lower housing 66. A horizontal threaded bore 108 extends through a side wall of the body 90 and communicates with the counterbore 104.

Figure 16:
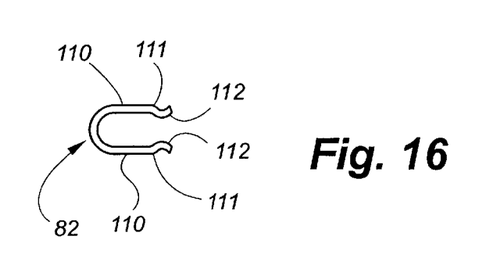
FIG. 16 is a top view of a retainer clip which snaps onto the mount of FIG. 12.

FIG. 16 illustrates the retainer clip 82. The retainer clip 82 is formed of a resilient material such as steel or nylon and includes a pair of arms 110. The arms 110 bend inward at a point 111 adjacent their free ends and then turn outward again, forming a pair of angled cam surfaces 112 which tend to bias the arms outward when the cam surfaces confront an object.

Figure 17:
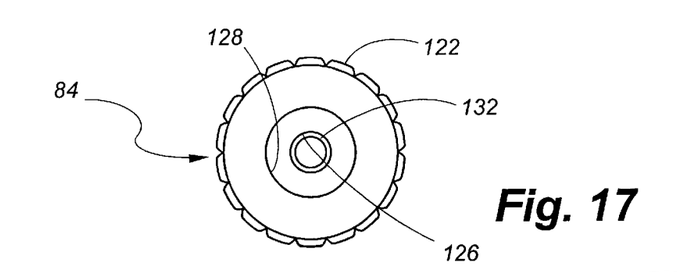
FIG. 17 is a front view of an adapter which engages the mount of FIG. 12.
Figure 18:
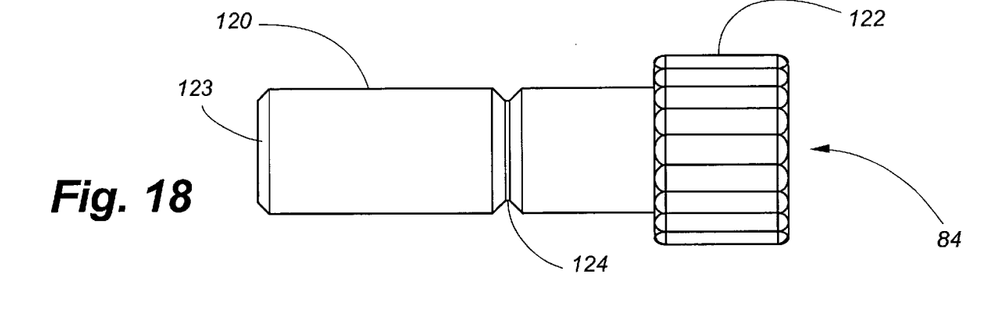
FIG. 18 is a side view of the adapter of FIG. 17.
Figure 19:
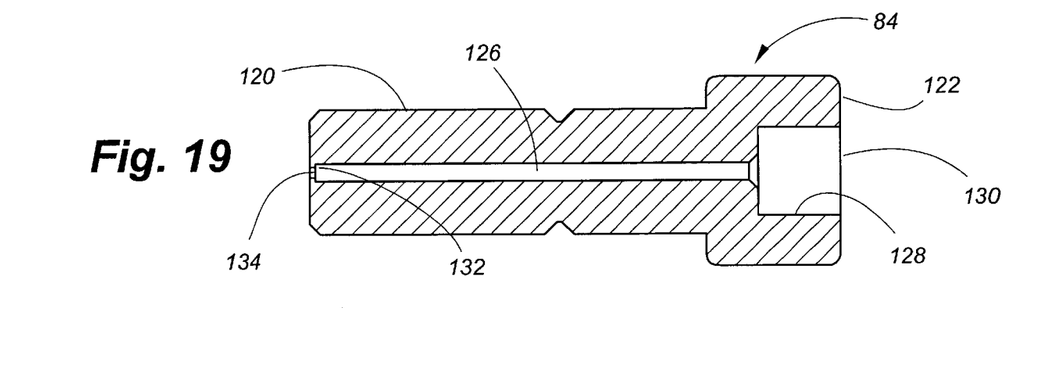
FIG. 19 is a side cutaway view of the adapter of FIG. 17.

Referring now to FIGS. 17–19, the adapter 84 includes a generally cylindrical elongated body portion 120 having an enlarged cylindrical boss 122 at one end. The opposite end of the body portion 120 has a chamfered lead-in 123. The peripheral surface of the boss 122 is knurled to facilitate gripping. The exterior surface of the elongated cylindrical body portion 120 has a V-shaped notch 124 extending around the periphery of the cylindrical body portion at an intermediate location. The outer diameter of the elongated cylindrical body portion 120 is dimensioned to fit snugly within the through bore 102 in the barrel 100 of the mount 76. The boss 122 at the forward end of the cylindrical body portion 120 has a larger diameter than the through bore 102 of the mount 76 and thus serves as a stop to limit the depth to which the adapter 84 can be inserted into the mount.

With particular reference now to FIG. 19, a longitudinal passageway 126 extends the length the cylindrical body portion 120 of the adapter 84. An enlarged counterbore 128 is formed in the forward end 130 of the adapter 84 coaxial with the passageway 126. At the rearmost end of the passageway 126, an annular stop 132 is formed. A small aperture 134 is provided in the central portion of the annular stop 132. The diameter of the passageway 126 is such as will receive the rearward end of the optical fiber 12 of the tissue localization device 10 therewithin. The aperture 134 of the annular stop 132 has a smaller diameter than the optical fiber 12, thus preventing the fiber from exiting the rearward end of the adapter 84.

Figure 20:
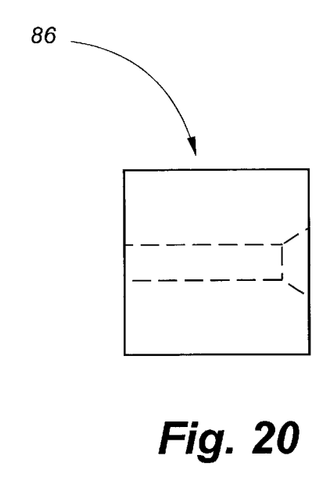
FIG. 20 is a side view of an optical fiber retention means in the form of a bushing which fits into the forward end of the adapter of FIG. 17.
Figure 21:
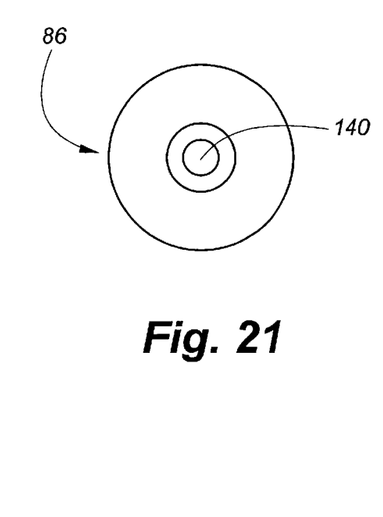
FIG. 21 is a front view of the bushing of FIG. 20.

Referring now to FIGS. 20 and 21, the cylindrical rubber bushing 86 includes a longitudinal passageway 140 having a diameter slightly smaller than the outer diameter of the optical fiber 12. The outer diameter of the bushing 86 is dimensioned to be received snugly within the counterbore 128 in the forward end of the adapter 84. The forward end of the passageway 140 flares outward to facilitate insertion of the rearward end of the optical fiber 12.

Figure 22:
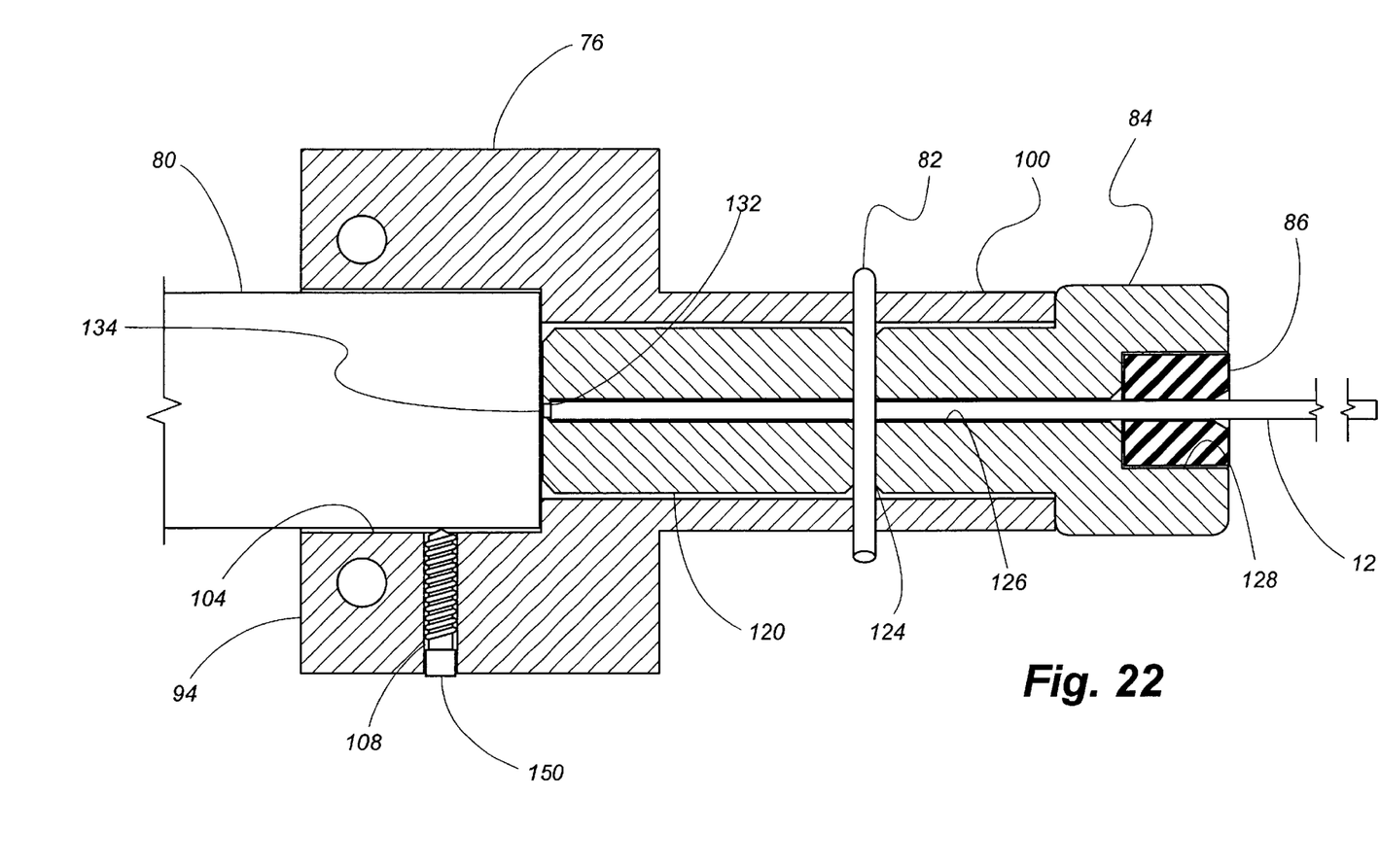
FIG. 22 is a top cutaway view of a laser, the adapter of FIG. 17, the bushing of FIG. 20, and the optical fiber of the tissue localization device of FIG. 4, all mounted to the mount of FIG. 12.

FIG. 22 shows the optical fiber 12 mounted to the adapter 84, with the adapter and the laser 80 assembled onto the mount 76. The cylindrical bushing 86 is fitted within the counterbore 128 in the forward end of the adapter 84. The rearward end of the optical fiber 12 is inserted through the rubber bushing 86 and through the longitudinal passageway 126 of the adapter 84 until it confronts the annular stop 132 at the rearward end of the adapter. The friction fit of the rubber bushing 86 around the periphery of the optical fiber 12 retains the optical fiber securely within the adapter 84. The rubber bushing 86 thus acts as a retention means for the optical fiber 12.

The cylindrical body portion 120 of the adapter 84 is inserted into the forward end of the barrel 100 of the mount 76. The retainer clip 82 is inserted over the barrel 100 of the mount 76 such that the arms 110 of the clip 82 protrude through the slots 105. The cam surfaces 112 anchor the clip 82 to the barrel 100. The cylindrical body portion 120 of the adapter 84 is inserted into the forward end of the barrel 100 until the arms 110 of the clip 82 engage the V-shaped notch 124 in the periphery of the adapter 84, locking the cylindrical body portion 120 in place. The boss 122 at the forward end of the cylindrical body portion 120 serves as a stop to limit the depth to which the adapter 84 can be inserted into the mount 76.

The forward (light emitting) end of the laser 80 is inserted into the counterbore 104 in the rearward face 94 of the mount 76 and advanced until the forward end of the laser rests on the base of the counterbore. A set screw 150 is threaded through the horizontal threaded bore 108 in the mount 76, the tip of the set screw clamping the laser 80 within the counterbore 104.

With the device thus assembled, the rearward end of the optical fiber 12 is disposed in the focal plane of the laser 80.

When the laser 80 is activated, the beam of light shines through the aperture 134 in the annular stop 132 at the rearward end of the adapter 84 and strikes the rearward end of the optical fiber 12. The light is then transmitted up the optical fiber 12 to the tip 14 (FIGS. 1 and 4–6), which illuminates to enable the surgeon to locate the tip of the tissue localization device 10, as hereinabove explained.

As will be appreciated, the strain relief tube 20 of the disclosed embodiment provides several advantages. First, because the hook members 24 are not bonded to an unreinforced tip, forces exerted by the hook members in response to movement of the optical fiber 12 while the hook members are anchored within tissue will not tend to break the tip off of the fiber. In addition, the strain relief tube 20 spreads the forces exerted by the hooks 24 over a larger area of the optical fiber 12, further contributing to the structural integrity of the device 10.

Finally, it will be understood that the preferred embodiment has been disclosed by way of example, and that other modifications may occur to those skilled in the art without departing from the scope and spirit of the appended claims.

What is claimed is:

1. An apparatus for marking a location within the tissue of a patient, comprising:

an optical fiber having a forward end, a rearward end, and an outer diameter, said forward end of said optical fiber being shaped into a tapered tip beginning at a transition point along the length of said optical fiber;

a strain relief tube disposed around said outer diameter of said optical fiber adjacent said forward end of said optical fiber; and anchor means for engaging the tissue of a patient to secure said tip of said optical fiber within the tissue of said patient, said anchor means being mounted to said strain relief tube, whereby said anchor means may be deployed to anchor said tip of said optical fiber in the vicinity of a location desired to be marked, and whereby said rearward end of said optical fiber may be optically coupled to a light source to transmit light through said optical fiber to illuminate said tip, thereby to facilitate a physician in visually locating said tip.

2. The apparatus of claim 1, wherein said anchor means is further mounted to said optical fiber.

3. The apparatus of claim 1, wherein said anchor means comprises at least one barb.

4. The apparatus of claim 1, wherein said tip of said optical fiber has a textured surface to disperse light transmitted down said optical fiber.

5. The apparatus of claim 1, wherein said strain relief tube is disposed over said transition point with at least a portion of said tip extending beyond said strain relief tube.

6. The apparatus of claim 1, further comprising a mount to which said light source and said rearward end of said optical fiber are each mounted so as to optically couple said light source to said optical fiber.

7. The apparatus of claim 6, further comprising an optical fiber retention means for physically coupling said rearward end of said optical fiber to said mount.

8. The apparatus of claim 6, further comprising an adapter which attaches to said rearward end of said optical fiber, said adapter engaging said light source to couple said optical fiber to said light source.

9. The apparatus of claim 8, further comprising an optical fiber retention means for physically coupling said rearward end of said optical fiber to said adapter.

* * * * *